United States Patent
Hu et al.

(10) Patent No.: US 12,282,022 B2
(45) Date of Patent: Apr. 22, 2025

(54) NANOPLASMONIC QUANTIFICATION OF TUMOR-DERIVED EXTRACELLULAR VESICLES IN PLASMA MICROSAMPLES FOR DETECTION AND TREATMENT MONITORING

(71) Applicant: THE METHODIST HOSPITAL, Houston, TX (US)

(72) Inventors: Ye Hu, Scottsdale, AZ (US); Jia Fan, Pearland, TX (US); Kai Liang, Beijing (CN); Fei Liu, Cupertino, CA (US); Dali Sun, Tempe, AZ (US)

(73) Assignee: THE METHODIST HOSPITAL, Houston, TX (US)

( * ) Notice: Subject to any disclaimer, the term of this patent is extended or adjusted under 35 U.S.C. 154(b) by 1171 days.

(21) Appl. No.: 16/469,082

(22) PCT Filed: Dec. 28, 2017

(86) PCT No.: PCT/US2017/068768
§ 371 (c)(1),
(2) Date: Jun. 12, 2019

(87) PCT Pub. No.: WO2018/126043
PCT Pub. Date: Jul. 5, 2018

(65) Prior Publication Data
US 2020/0096516 A1     Mar. 26, 2020

Related U.S. Application Data

(60) Provisional application No. 62/440,494, filed on Dec. 30, 2016.

(51) Int. Cl.
*G01N 33/574*     (2006.01)
*G01N 33/543*     (2006.01)

(52) U.S. Cl.
CPC .  *G01N 33/57438* (2013.01); *G01N 33/54346* (2013.01)

(58) Field of Classification Search
CPC .................................................. G01N 33/57438
See application file for complete search history.

(56) References Cited

U.S. PATENT DOCUMENTS

2016/0003835 A1*  1/2016  Halbert .............. G01N 33/5308
                                                                      506/9
2019/0234952 A1    8/2019  Hu

FOREIGN PATENT DOCUMENTS

WO       2015084800 A1    6/2015
WO       2017053516 A1    3/2017

OTHER PUBLICATIONS

Q. Chang et al. Effects of dasatinib on EphA2 receptor tyrosine Kinase act downstream signalling in pancreatic cancer, British J of Cancer, 99, 1074-1082. (Year: 2006).*
Greg J Nusz et al. Label-Gree Plasmonic Detection of Biuomolecular Binding by a single Gold Nanorod, Anal Chem. 80, 984-989. (Year: 2008).*
Yusuke Yoshioka et al., Comparative marker analysis of extracellular vesicles in different human cancer types, Journal of Extracellular Vesicles, 2:1, 20424 (Year: 2013).*
Greg J Nusz et al., Label-Free Plasmonic Detection of Biomolecular Binding by a single Gold Nanorod, Anal Chem. 80,984-989. (Year: 2008).*
Kai Liang et al., Nature Biomedical Engineering, 1, Article No. 0021. (Year: 2017).*
Raposo G, et al. Extracellular vesicles: exosomes, microvesicles, and friends. J Cell Biol. 2013; 200:373-383. [PubMed: 23420871].
Rodriguez-Lorenzo L, et al. Plasmonic nanosensors with inverse sensitivity by means of enzyme-guided crystal growth. Nat Mater. 2012; 11:604-607. [PubMed: 22635043].
Shao H, et al. Chip-based analysis of exosomal mRNA mediating drug resistance in glioblastoma. Nat Commun. 2015; 6:6999. [PubMed: 25959588].
Shao H, et al. Protein typing of circulating microvesicles allows real-time monitoring of glioblastoma therapy. Nat Med. 2012; 18:1835-1840. [PubMed: 23142818].
Shi L, et al. Plasmon resonance scattering spectroscopy at the single-nanoparticle level: real-time monitoring of a click reaction. Angew Chem Int Ed Engl. 2013; 52:6011-6014. [PubMed: 23616358].
Tanaka Y, et al. Clinical impact of serum exosomal microRNA-21 as a clinical biomarker in human esophageal squamous cell carcinoma. Cancer. 2013; 119:1159-1167. [PubMed: 23224754].
Thery C, et al. Exosomes: composition, biogenesis and function. Nat Rev Immunol. 2002; 2:569-579. DOI: 10.1038/hri855 [PubMed: 12154376].
Théry C, et al. Isolation and characterization of exosomes from cell culture supernatants and biological fluids. Curr Protoc Cell Biol. 2006:3.22.21-23.22.29. [PubMed: 18228482].
Vaidyanathan R, et al. Detecting exosomes specifically: a multiplexed device based on alternating current electrohydrodynamic induced nanoshearing. Anal Chem. 2014; 86:11125-11132. [PubMed: 25324037].
Van Der Pol E, et al. Classification, functions, and clinical relevance of extracellular vesicles. Pharmacol Rev. 2012; 64:676-705. [PubMed: 22722893].
Yokoi K, et al. Porous silicon nanocarriers for dual targeting tumor associated endothelial cells and macrophages in stroma of orthotopic human pancreatic cancers. Cancer Lett. 2013; 334:319-327. [PubMed: 23000514].

(Continued)

*Primary Examiner* — Jake M Vu
*Assistant Examiner* — Jagadishwar R Samala
(74) *Attorney, Agent, or Firm* — Quarles & Brady, LLP

(57) ABSTRACT

A rapid, ultrasensitive and inexpensive nanoplasmon-enhanced scattering (nPES) assay that directly quantifies tumor-derived EVs from as little as 1 μ[|$]$¨$$[|$] $¨AÄ[|$]$¨gï, of plasma is described herein. This assay uses binding of gold nanospheres and nanorods with EV- and tumor-derived EV-specificities to produce a local plasmon effect that enhances tumor-derived EV detection sensitivity and specificity. This nPES approach is also a noninvasive method for assessing pancreatic cancer stage and treatment response that can be easily refined for clinical use, and is readily adapted for diagnosis and monitoring of other conditions with disease-specific EV proteins.

8 Claims, 5 Drawing Sheets

(56) References Cited

OTHER PUBLICATIONS

Yoshioka Y, et al. Ultra-sensitive liquid biopsy of circulating extracellular vesicles using ExoScreen. Nat Commun. 2014; 5:3591. [PubMed: 24710016].

Yoshioka, Y, et al. "Comparative marker analysis of extracellular vesicles in different human cancer types." Journal of extracellular vesicles 2.1 (2013): 20424.

Chang, Q., et al., "Effects of dasatinib on EphA2 receptor tyrosine kinase activity and downstream signalling in pancreatic cancer," British Journal of Cancer, vol. 99, published online Sep. 16, 2018, pp. 1074-1082.

International Search Report and Written Opinion issued for International Application No. PCT/US2017/068768, mail date Mar. 5, 2018, 11 pages.

Anderson HC, et al. Role of extracellular membrane vesicles in the pathogenesis of various diseases, including cancer, renal diseases, atherosclerosis, and arthritis. Lab Invest. 2010; 90:1549-1557. [PubMed: 20805791].

Anker JN, et al. Biosensing with plasmonic nanosensors. Nat Mater. 2008; 7:442-453. [PubMed: 18497851].

Ansuini H, et al. Anti-EphA2 Antibodies with Distinct In Vitro Properties Have Equal In Vivo Efficacy in Pancreatic Cancer. J Oncol. 2009; 2009:951917. [PubMed: 20130824].

Archin NM, et al. Administration of vorinostat disrupts HIV-1 latency in patients on antiretroviral therapy. Nature. 2012:487.

Ballehaninna UK, et al. Biomarkers for pancreatic cancer: promising new markers and options beyond CA 19-9. Tumour Biol. 2013; 34:3279-3292. [PubMed: 23949878].

Ballehaninna UK, et al. The clinical utility of serum CA 19-9 in the diagnosis, prognosis and management of pancreatic adenocarcinoma: An evidence based appraisal. J Gastrointest Oncol. 2012; 3:105-119. [PubMed: 22811878].

Boukouris S, et al. Exosomes in bodily fluids are a highly stable resource of disease biomarkers. Proteomics Clin Appl. 2015; 9:358-367. [PubMed: 25684126].

Brantley DM, et al. Soluble EphA receptors inhibit tumor angiogenesis and progression in vivo. Oncogene. 2002; 21:7011-7026. [PubMed: 12370823].

Brinton LT, et al. Formation and role of exosomes in cancer. Cell Mol Life Sci. 2015; 72:659-671. [PubMed: 25336151].

Choi Y, et al. Selective and sensitive detection of metal ions by plasmonic resonance energy transfer-based hanospectroscopy. Nat Nanotechnol. 2009; 4:742-746. [PubMed: 19893511].

De Candia P, et al. Intracellular modulation, extracellular disposal and serum increase of MiR-150 mark lymphocyte activation. PLoS One. 2013; 8:e75348. [PubMed: 24205408].

Del Villano BC, et al. Radioimmunometric assay for monoclonal antibody-defined tumor marker, CA 19-9. Clin Chem. 1983; 29:549-552. [PubMed: 6825270].

Dobrzanski P, et al. Antiangiogenic and antitumor efficacy of EphA2 receptor antagonist. Caner Research. 2004; 64:910-919.

Duxbury MS, et al. EphA2: a determinant of malignant cellular behavior and a potential therapeutic target in pancreatic adenocarcinoma. Oncogene. 2004; 23:1448-1456. [PubMed: 14973554].

Duxbury MS, et al. Ligation of EphA2 by Ephrin A1-Fc inhibits pancreatic adenocarcinoma cellular invasiveness. Biochem Biophys Res Commun. 2004; 320:1096-1102. [PubMed: 15249202].

Evans DB, et al. Preoperative chemoradiation and pancreaticoduodenectomy for adenocarcinoma of the pancreas. Arch Surg. 1992; 127:1335-1339. [PubMed: 1359851].

Freelove R, et al. Pancreatic Cancer: Diagnosis and Management. Am Fam Physician. 2006; 73:485-492. [PubMed: 16477897].

Ghosh SK, et al. Interparticle coupling effect on the surface plasmon resonance of gold nanoparticles: from theory to applications. Chem Rev. 2007; 107:4797-4862. [PubMed: 17999554].

Good DM, et al. Body fluid proteomics for biomarker discovery: lessons from the past hold the key to success in the future. J Proteome Res. 2007; 6:4549-4555. [PubMed: 17970587].

Gyorgy B, et al. Membrane vesicles, current state-of-the-art: emerging role of extracellular vesicles. Cell Mol Life Sci. 2011; 68:2667-2688. [PubMed: 21560073].

He M, et al. Integrated immunoisolation and protein analysis of circulating exosomes using microfluidic technology. Lab Chip. 2014; 14:3773-3780. [PubMed: 25099143].

Hidalgo M. Pancreatic cancer. N Engl J Med. 2010:362.

Hori SS, et al. Mathematical model identifies blood biomarker-based early cancer detection strategies and imitations. Sci Transl Med. 2011; 3:1-9.

Im H, et al. Label-free detection and molecular profiling of exosomes with a nano-plasmonic sensor. Nat Biotechnol. 2014; 32:490-495. [PubMed: 24752081].

Jazieh KA, et al. The clinical utility of biomarkers in the management of pancreatic adenocarcinoma. Semin Radiat Oncol. 2014; 24:67-76. [PubMed: 24635863].

Jensen MM, et al. Tumor vol. in subcutaneous mouse xenografts measured by microCT is more accurate and reproducible than determined by 18F-FDG-microPET or external caliper. BMC Med Imaging. 2008; 8:16. [PubMed: 18925932].

Joshi GK, et al. Label-free nanoplasmonic-based short noncoding RNA sensing at attomolar concentrations allows for quantitative and highly specific assay of microRNA-10b in biological fluids and circulating exosomes. ACS Nano. 2015; 9:11075-11089. [PubMed: 26444644].

Kalra H, et al. Comparative proteomics evaluation of plasma exosome isolation techniques and assessment of the stability of exosomes in normal human blood plasma. Proteomics. 2013; 13:3354-3364. [PubMed: 24115447].

Kanwar SS, et al. Microfluidic device (ExoChip) for on-chip isolation, quantification and characterization of circulating exosomes. Lab Chip. 2014; 14:1891-1900. [PubMed: 24722878].

Khan S, et al. Plasma-derived exosomal survivin, a plausible biomarker for early detection of prostate cancer. PLoS One. 2012; 7:e46737. [PubMed: 23091600].

Kinch, MS et al. Overexpression and functional alterations of the EphA2 tyrosine kinase in cancer. Clin Exp Metastasis. 2003; 20:59-68. [PubMed: 12650608].

Kowal J, et al. Proteomic comparison defines novel markers to characterize heterogeneous populations of extracellular vesicle subtypes. Proc Natl Acad Sci. 2016; 113:E968-977. [PubMed: 26858453].

Lane RE, et al. Analysis of exosome purification methods using a model liposome system and tunable-resistive pulse sensing. Sci Rep. 2015; 5:7639. [PubMed: 25559219].

Lee K, et al. Quantitative imaging of single mRNA splice variants in living cells. Nat Nanotechnol. 2014; 9:474-480. [PubMed: 24747838].

Lescuyer P, et al. How shall we use the proteomics toolbox for biomarker discovery? J Proteome Res. 2007; 6:3371-3376. [PubMed: 17655344].

Li D, et al. Pancreatic cancer. The Lancet. 2004; 363:1049-1057.

Link S, et al. Spectral properties and relaxation dynamics of surface plasmon electronic oscillations in gold and silver hanodots and nanorods. J Phys Chem B. 1999; 103:8410-8426.

Locker GY, et al. ASCO 2006 update of recommendations for the use of tumor markers in gastrointestinal cancer. J Clin Oncol. 2006; 24:5313-5327. [PubMed: 17060676].

Logozzi M, et al. High levels of exosomes expressing CD63 and caveolin-1 in plasma of melanoma patients. PLoS One. 2009; 4:e5219. [PubMed: 19381331].

Logsdon CD, et al. Molecular profiling of pancreatic adenocarcinoma and chronic pancreatitis identifies multiple genes differentially regulated in pancreatic cancer. Cancer Res. 2003; 63:2649-2657. [PubMed: 12750293].

Lowenfels AB, et al. Pancreatitis and the risk of pancreatic cancer. N Engl J Med. 1993; 328:1433-1437. [PubMed: 8479461].

Melo SA, et al. Glypican-1 identifies cancer exosomes and detects early pancreatic cancer. Nature. 2015; 523:177-182. [PubMed: 26106858].

Miyazaki T, et al. EphA2 overexpression correlates with poor prognosis in esophageal squamous cell carcinoma. Int J Cancer. 2003; 103:657-663. [PubMed: 12494475].

Mudali SV, et al. Patterns of EphA2 protein expression in primary and metastatic pancreatic carcinoma and correlation with genetic status. Clin Exp Metastasis. 2006; 23:357-365. [PubMed: 17146615].

(56) References Cited

OTHER PUBLICATIONS

Muralidharan-Chari V, et al. Microvesicles: mediators of extracellular communication during cancer progression. J Cell Sci. 2010; 123:1603-1611. [PubMed: 20445011].

Nusz GJ, et al. Label-free plasmonic detection of biomolecular binding by a single gold nanorod. Anal Chem. 2008; 80:984-989. [PubMed: 18197636].

O'Driscoll L. Expanding on exosomes and ectosomes in cancer. N Engl J Med. 2015:372.

Pei H, et al. FKBP51 affects cancer cell response to chemotherapy by negatively regulating Akt. Cancer Cell. 2009; 16:259-266. [PubMed: 19732725].

Peinado H, et al. Melanoma exosomes educate bone marrow progenitor cells toward a prometastatic phenotype through MET. Nat Med. 2012; 18:883-891. [PubMed: 22635005].

Rabinowits G, et al. Exosomal microRNA: a diagnostic marker for lung cancer. Clin Lung Cancer. 2009; 10:42-46. [PubMed: 19289371].

Oldenburg et al., "Topics in Fluorescence Spectroscopy vol. 8 Radiative Decay Engineering", Geddes, Springer, 333-346, 2005.

\* cited by examiner

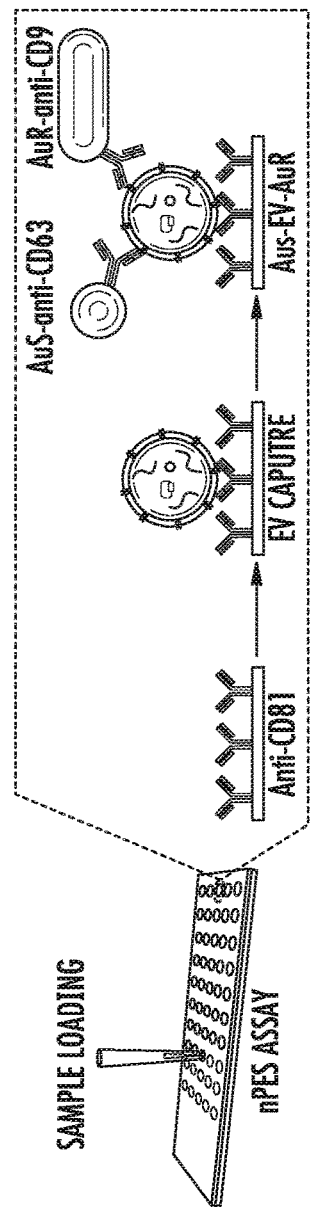
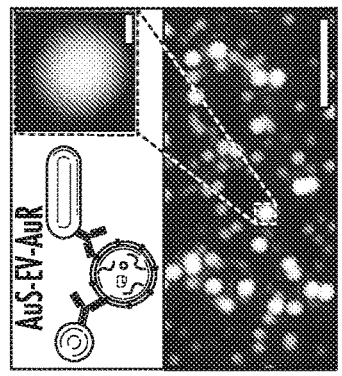
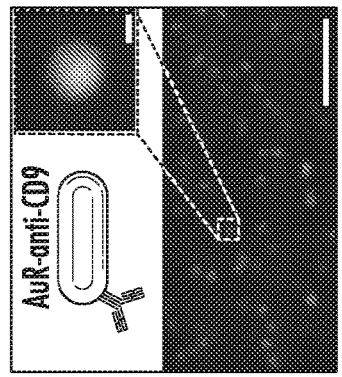
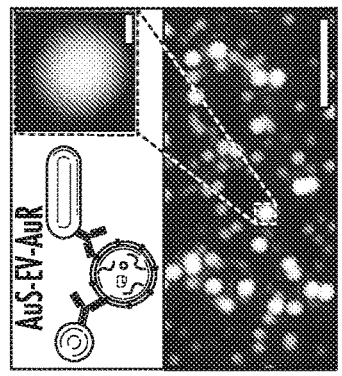
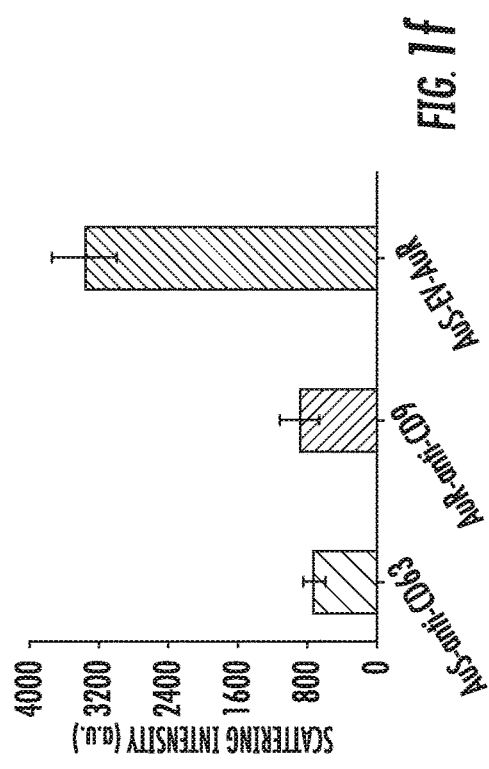
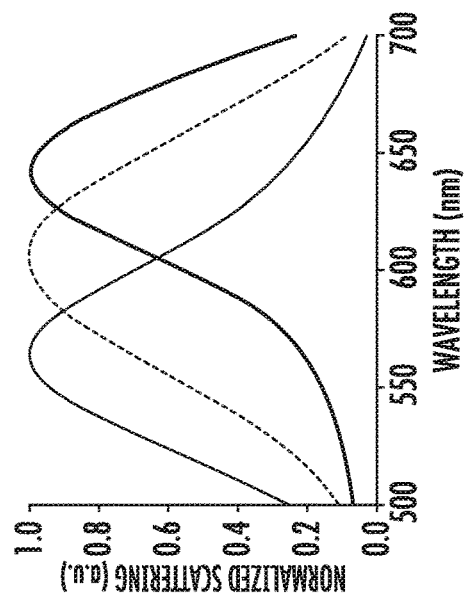
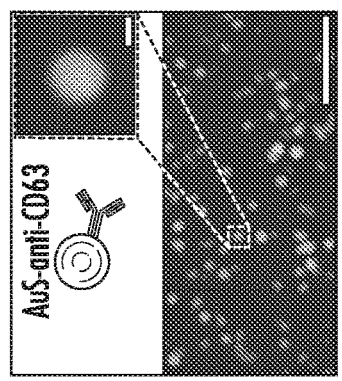

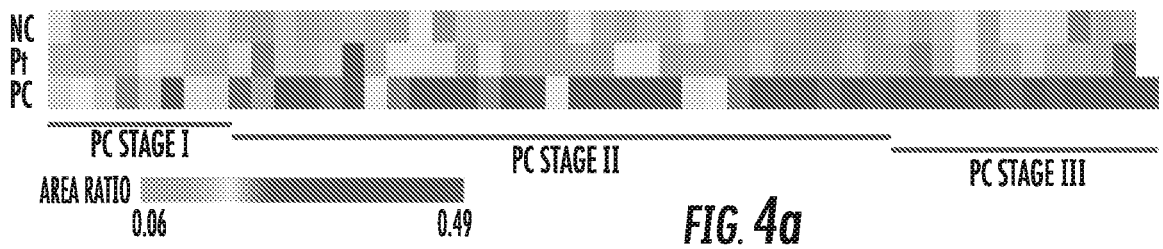
FIG. 4a
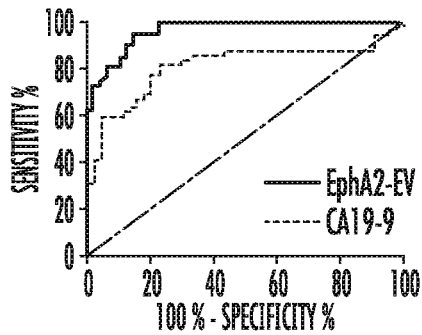
FIG. 4b
| | PC vs. NC | | | |
|---|---|---|---|---|
| | AUC*** (95 % CI) | CUTOFF | SENSITIVITY* (95 % CI) | SPECIFICITY (95 % CI) |
| CA19-9 | 0.81 (0.72 - 0.90) | > 20.60 | 81% (67% - 91%) | 77% (62% - 88%) |
| EphA2-EV | 0.96 (0.93 - 0.99) | > 0.1668 | 94% (85% - 98%) | 85% (72% - 93%) |
FIG. 4c
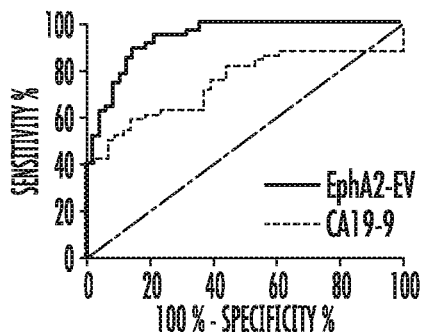
FIG. 4d
| | PC vs. Pt | | | |
|---|---|---|---|---|
| | AUC*** (95 % CI) | CUTOFF | SENSITIVITY*** (95 % CI) | SPECIFICITY (95 % CI) |
| CA19-9 | 0.74 (0.64 - 0.84) | > 44.04 | 61% (46% - 74%) | 81% (66% - 91%) |
| EphA2-EV | 0.96 (0.89 - 0.98) | > 0.1724 | 89% (79% - 96%) | 85% (72% - 93%) |
FIG. 4e
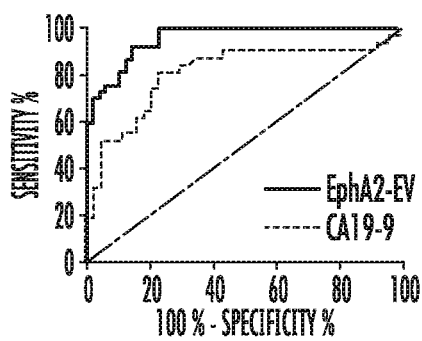
FIG. 4f
| | PC STAGE (I+II) vs. NC | | | |
|---|---|---|---|---|
| | AUC*** (95 % CI) | CUTOFF | SENSITIVITY* (95 % CI) | SPECIFICITY (95 % CI) |
| CA19-9 | 0.81 (0.69 - 0.91) | > 20.60 | 80% (62% - 92%) | 77% (62% - 88%) |
| EphA2-EV | 0.96 (0.91 - 0.99) | > 0.1668 | 91% (78% - 98%) | 85% (72% - 93%) |
FIG. 4g

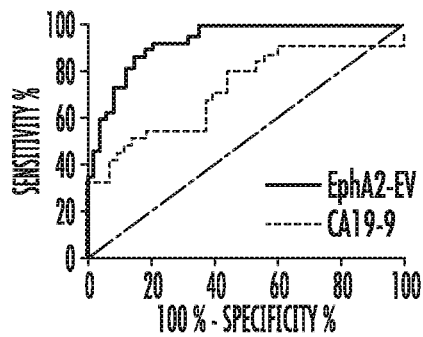
FIG. 4h
| | PC STAGE (I+II) vs. Pt | | | |
|---|---|---|---|---|
| | AUC*** (95 % CI) | CUTOFF | SENSITIVITY (95 % CI) | SPECIFICITY*** (95 % CI) |
| CA19-9 | 0.72 (0.59 - 0.84) | >19.72 | 81% (62% - 92%) | 56% (39% - 70%) |
| EphA2-EV | 0.93 (0.87 - 0.97) | >0.1724 | 86% (71% - 95%) | 85% (72% - 93%) |
FIG. 4i
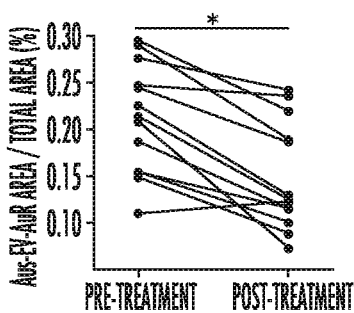
FIG. 4j
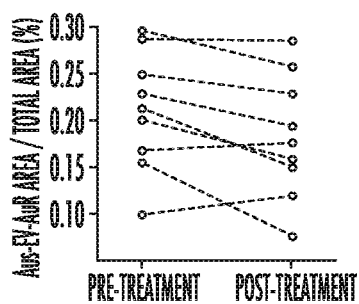
FIG. 4k
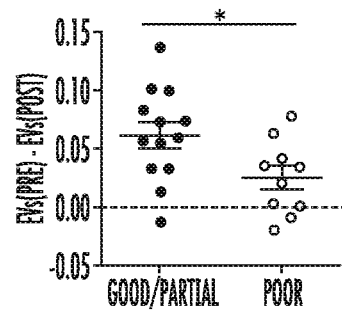
FIG. 4l

NANOPLASMONIC QUANTIFICATION OF TUMOR-DERIVED EXTRACELLULAR VESICLES IN PLASMA MICROSAMPLES FOR DETECTION AND TREATMENT MONITORING

CROSS-REFERENCE TO RELATED APPLICATIONS

This application represents the national stage entry of International Application No. PCT/US2017/068768, filed on Dec. 28, 2017, and claims priority to U.S. Provisional Patent Application No. 62/440,494 filed on Dec. 30, 2016, the disclosures of which are incorporated herein in their entirety by reference.

STATEMENT REGARDING FEDERALLY SPONSORED RESEARCH OR DEVELOPMENT

This invention was made with government support under RO1 AI113725 and RO1 AI122932 awarded by the National Institutes of Health. The government has certain rights in the invention.

BACKGROUND

Extracellular vesicles (EVs), including exosomes and other membranous vesicles, are abundantly secreted into the extracellular space by most cells from where they can ultimately accumulate in the circulation. EVs actively participate in tumor initiation, progression, and metastasis, shuttle signaling molecules (proteins and nucleic acids) that reflect their parental cell and tissue origins.

Circulating tumor-derived EVs thus hold great potential to detect cancer in a noninvasive manner, however, translating tumor EVs into cancer detecting assays has been challenging due to the lack of 1) simple methods for EV analysis and 2) molecular targets that distinguish tumor derived EVs from normal EVs. Conventional detection technologies require time consuming and labor-intensive isolation and purification procedures (e.g., ultracentrifugation, immunomagnetic enrichment, multi-step filtration or microfluidic-based separation) followed by EV quantification and/or analyses of EV carrying molecular contents (e.g., mRNA, miRNA, and proteins). These techniques are impractical for clinical and research use since they require relatively large sample volumes and are complex, low-throughput, expensive and have long turnaround times. Sample requirements are a particular barrier to animal-based research studies, since the blood volume available from common mouse models of human disease is very limited and precludes longitudinal studies. EV-enriched membrane proteins (e.g., CD9, CD63, and CD81) used for standard EV analyses are present on EVs derived from most cell types, but currently very few EV proteins have been proposed to associate with different types of cancers.

SUMMARY

Embodiments of the current technology disclose a method for detecting a cancer specific protein. The method comprises contacting an EV containing sample with a surface conjugated with a first antibody directed to an EV molecule to separate said EV from the EV containing sample; removing the EV containing sample from the surface; incubating the surface with a first set of nanoparticles conjugated with a second antibody directed to the cancer specific protein; and detecting whether said cancer specific protein is present in the EV containing sample by detecting binding between the second antibody and the EV. The contacting step further comprises conjugating the surface with the first antibody directed to an EV molecule. In certain embodiments, the EV protein is selected from the group consisting of CD63, CD81, CD9, CD24, CD, 26, CD10, tumor susceptibility gene 101(TSG101), heat shock 70 kDa protein 4 (HSP70), Rab-5b, programmed cell death 6-interacting protein (AIP1/Alix), aquaporin 2 (AQP2), vascular endothelial growth factor receptor 1 (FLT1), N-glycan containing a fucose residue, phosphocholine, phosphatidylserine, and sphingomyelin.

The incubating step further comprises incubating the surface with a second set of nanoparticles conjugated with a third antibody directed to an EV molecule, wherein the EV protein is selected from the group consisting of CD63, CD81, CD9, CD24, CD, 26, CD10, TSG101, HSP70, Rab-5b, AIP1/Alix, AQP2, FLT1, N-glycan containing a fucose residue, phosphocholine, phosphatidylserine, and sphingomyelin; and the nanoparticles comprises a plurality of nanospheres, a plurality of nanorods, or a combination thereof. The detecting step further comprises detecting binding between the second antibody directed to the cancer specific protein and the EV; and detecting binding between the third antibody directed to an EV molecule and the EV. Moreover, the detecting step further comprises forming an EV complex comprising an EV, a first nanoparticle binding to the EV via the second antibody, and a second nanoparticle binding to the EV via a third antibody, wherein the first nanoparticle can interact with the second nanoparticle to produce nanoplasmons when a certain distance between the first nanoparticle and the second nanoparticle is reached; and detecting said nanoplasmons.

Moreover, an embodiment of the current technology relates to a method for detecting a pancreatic cancer specific protein, ephrin type-A receptor 2 (EphA2), comprising contacting an extracellular vesicle (EV) containing sample with a surface conjugated with a first antibody directed to an EV molecule to separate said EV from the EV containing sample; removing the EV containing sample from the surface; incubating the surface with a first set of nanoparticles conjugated with a second antibody directed to EphA2 to obtain a pancreatic cancer derived EV; and detecting whether EphA2 is present in the EV containing sample by detecting binding between the second antibody and the pancreatic cancer derived EV.

The contacting step further comprises conjugating the surface with the first antibody directed to an EV molecule, wherein the EV molecule is selected from the group consisting of CD63, CD81, CD9, CD24, CD, 26, CD10, TSG101, HSP70, Rab-5b, AIP1/Alix, AQP2, FLT1, N-glycan containing a fucose residue, phosphocholine, phosphatidylserine, and sphingomyelin. Further, the incubating step comprises incubating the surface with a second set of nanoparticles conjugated with a third antibody directed to an EV molecule, wherein the EV molecule is selected from the group consisting of CD63, CD81, CD9, CD24, CD, 26, CD10, TSG101, HSP70, Rab-5b, AIP1/Alix, AQP2, FLT1, N-glycan containing a fucose residue, phosphocholine, phosphatidylserine, and sphingomyelin; and the nanoparticles comprises a plurality of nanospheres, a plurality of nanorods, or a combination thereof. The detecting step further comprises detecting binding between the second antibody directed to EphA2 and the pancreatic cancer derived EV; and detecting binding between the third antibody directed to an EV molecule and the pancreatic cancer derived EV. Additionally, the detecting step further comprises forming an EV complex comprising an EV, a first nanoparticle binding to the EV via the second antibody directed to EphA2, and a second nanoparticle binding to the EV via a third antibody, wherein the first nanoparticle can interact with the second nanoparticle to produce nanoplasmons when a certain distance between the first nanoparticle and the second nanoparticle is reached; and detecting said nanoplasmons.

In addition, an embodiment of the current technology relates to a method for diagnosing pancreatic cancer in a subject, comprising contacting an extracellular vesicle (EV) containing sample with a surface conjugated with a first antibody directed to an EV protein to separate said EV from the EV containing sample; removing the EV containing sample from the surface; incubating the surface with a first set of nanoparticles conjugated with a second antibody directed to EphA2 to obtain a pancreatic cancer derived EV; and detecting whether EphA2 is present in the EV containing sample by detecting binding between the second antibody and the pancreatic cancer derived EV. The contacting step further comprises conjugating the surface with the first antibody directed to an EV protein, wherein the EV protein is selected from the group consisting of CD63, CD81, CD9, TSG101, HSP70, Rab-5b, AIP1/Alix, AQP2, and FLT1. The incubating step further comprises incubating the surface with a second set of nanoparticles conjugated with a third antibody directed to an EV protein, wherein the EV protein is selected from the group consisting of CD63, CD81, CD9, TSG101, HSP70, Rab-5b, AIP1/Alix, AQP2, and FLT1; and the nanoparticles comprises a plurality of nanospheres, a plurality of nanorods, or a combination thereof. The detecting step further comprises detecting binding between the second antibody directed to EphA2 and the pancreatic cancer derived EV; and detecting binding between the third antibody directed to an EV protein and the pancreatic cancer derived EV. Additionally, the detecting step further comprises forming an EV complex comprising an EV, a first nanoparticle binding to the EV via the second antibody directed to EphA2, and a second nanoparticle binding to the EV via a third antibody, wherein the first nanoparticle can interact with the second nanoparticle to produce nanoplasmons when a certain distance between the first nanoparticle and the second nanoparticle is reached; and detecting said nanoplasmons.

BRIEF DESCRIPTION OF DRAWINGS

FIG. 1. Design of an nanoplasmon-enhanced scattering (nPES) platform for EV detection. (a) Schematic overview of the nPES assay for specific detection of EVs. (b-d) Dark-Field Microscope (DFM) images of Au nanosphere particles (AuS)-anti-CD63 (green dots), Au nanopod particles (AuR)-anti-CD9 (red dots), and the AuS-EV-AuR complexes are detectable as bright yellow dots. Scale bars: 2 μm (100 nm for magnified image). (e) Scattering spectra and (f) intensities of AuS-anti-CD63 48, AuR-anti-CD9 (red), and AuS-EV-AuR (yellow) complexes. The scattering spectra and related intensities were recorded from 10 random-selected particles by a spectrograph CCD equipped with a monochromator (CASCADE 512B, Roper Scientific.). Data represent means±SEM; n=10 replicates/sample.

FIG. 4. EphA2-EV detection and clinical performance. 827 (a) Comparison of EphA2-EV levels in plasma samples from normal control (NC; n=48), chronic pancreatitis (Pt; n=48) and PC (n=49: 8 stage I, 29 stage II, and 12 stage III) patients. (b, d, f, h) ROC curves and (c, e, g, i) AUCs, sensitivities, and specificities of EphA2-EV and CA19-9 for PC diagnosis. EphA2-EV levels before and after neoadjuvant therapy in PC patients who revealed (j) good/partial (n=13) or (k) poor responses (n=10) to therapy and (1) the relative pre-to-post therapy differences of these groups. Data represent means±SEM; n=3 replicates/sample, *p<0.05 by two-sided t-test (j) or paired t-test (1). Researchers performing these analyses were not blinded to sample identity.

DESCRIPTION

Figure 2B:
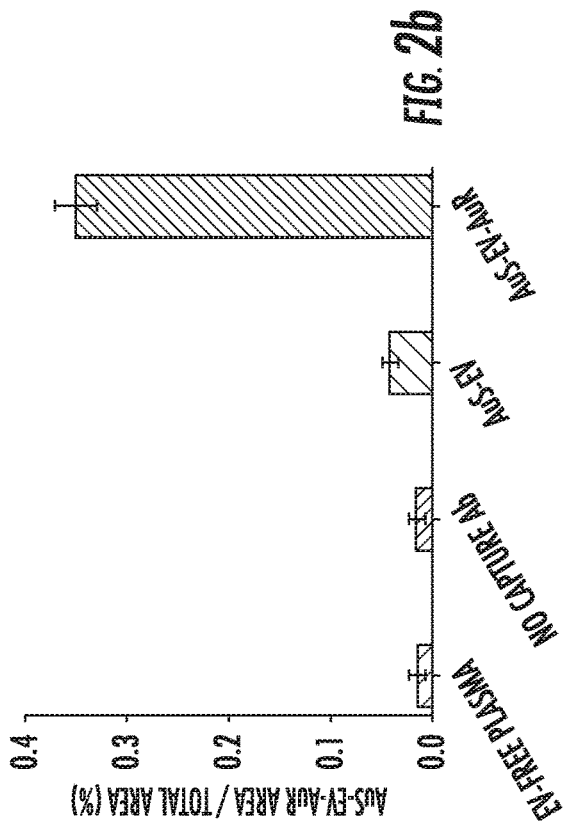
FIG. 2. Characterization of nPES assay performance with exosome-spiked human plasma samples. (a) Dark field Microscope (DFM) images and (b) area ratios of Gold nanoparticles (GNP) signal in negative (EV-free plasma, no capture Ab and AuS-EV single labeling) controls vs. nPES assay (AuS-EV-AuR complexes) samples. (c) DFM images of AuS-EV-AuR complexes detected in plasma samples spiked with the indicated EV concentrations. (d) Correlation of AuS-EV spiked plasma samples. All dark field images were analyzed by NIH IMAGE J image analysis software at a pixel intensity threshold of 255. Data represent means±SEM; n=3/group.

A problem of translating tumor EVs into cancer protein markers is addressed by the current technology of developing a system and a method to quantify and detect tumor-derived EVs from a small volume sample in a rapid, ultrasensitive, and inexpensive manner.

This technology disclosed herein is described in one or more exemplary embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present technology disclosed herein. Thus, appearances of the phrases "in one embodiment," "in an embodiment," and similar language throughout this specification may, but do not necessarily, all refer to the same embodiment.

The described features, structures, or characteristics of the technology disclosed herein may be combined in any suitable manner in one or more embodiments. In the following description, numerous specific details are recited to provide a thorough understanding of embodiments of the technology disclosed herein. One skilled in the relevant art will recognize, however, that the technology disclosed herein may be practiced without one or more of the specific details, or with other methods, components, materials, and so forth. In other instances, well-known structures, materials, or operations are not shown or described in detail to avoid obscuring aspects of the technology disclosed herein.

For the terms "for example" and "such as," and grammatical equivalents thereof, the phrase "and without limitation" is understood to follow unless explicitly stated otherwise. As used herein, the term "about" is meant to account for ±10% in any measuring variations due to experimental error. Numerical result of any measurement disclosed below is understood to be modified by the term "about," whether or not the term is explicitly used and unless explicitly stated otherwise.

Recently, methods have been developed to isolate tumor derived EVs by capturing candidate tumor-regulated markers on the EV membrane but the clinical utility of EVs as cancer biomarkers is still very limited since most proposed methods require time-consuming EV isolation steps prior to the actual analysis. Assays useful in clinical settings generally share several features in common. Most are rapid, highly sensitive and specific, require minimal processing and are usually amenable to automation.

To address those aforementioned issues and to comport with clinical usefulness, in certain embodiments, a rapid nanoparticle based EV assay is developed and is described herein in which EVs present in small volumes of biological samples containing EVs were captured by an EV-specific antibody on the surface of a sensor chip, and then hybridized with two antibody-conjugated nanoparticle probes. Dual binding of EVs by the two nanoparticle probes produced a local plasmon to increase scattering intensity and shift its wavelength, resulting in a marked increase in the sensitivity and specificity of EV detection. In some embodiments, an EV containing sample could be unprocessed plasma samples containing EVs. In other embodiments, an EV containing sample could be urine samples containing EVs. In certain embodiments, a surface of a sensor chip is glass. In other embodiments, a surface of a sensor chip comprises silica. In yet other embodiments, a surface of a sensor chip comprises functional polysaccharides, such as chitosan, cellulose, or other suitable functional polysaccharides. In certain embodiments, an EV-specific antibody is used to detect an EV specific marker. An EV specific marker is selected from the group consisting of CD63, CD81, CD9, tumor susceptibility gene 101(TSG101), heat shock 70 kDa protein 4 (HSP70), Rab-5b, programmed cell death 6-interacting protein (AIP1/Alix), aquaporin 2 (AQP2), and vascular endothelial growth factor receptor 1 (FLT1). In certain embodiments, the EV specific markers include other membrane molecules on EV surface, such as, among others, membrane proteins CD24, CD26, and CD10 and, N-glycan containing a fucose residue attached to EVs, and phospholipids such as phosphocholine, phosphatidylserine, sphingomyelin, and etc. attached to EVs.

Comparative and quantitative proteomic analyses of EVs derived from normal and tumor-derived pancreatic cells lines identified candidate biomarkers that were selectively enriched on EVs of pancreatic cancer (PC) cells, including ephrin type-A receptor 2 (EphA2), which is enriched on several tumors and plays critical roles in cancer progression, metastasis and prognosis. Other methods known to a person of ordinary skill in the art can be used to identify other potential EV cancer protein biomarkers for other types of cancers. EphA2 overexpression is reported to increase in vitro invasiveness and anoikis resistance of pancreatic adenocarcinoma cell lines, while in vitro EphA2 knockdown has the opposite effect and EphA2 siRNA treatment decreases mouse PC tumor growth and metastases in parallel with increased tumor-associated apoptosis. Other Substituting an EphA2-specific nanoparticle for one of the two EV-specific nanoparticles in the nanoplasmon-enhanced scattering (nPES) method produced a blood-based EphA2-EV nPES assay that demonstrated strong diagnostic sensitivity and specificity for PC patients in a pilot study performed with cohorts of normal healthy control (NC) subjects, pancreatitis patients and PC patients with stage I-III cancer. Other identified EV cancer protein biomarkers can be used to form EV cancer biomarker-specific nanoparticles to replace one EV-specific nanoparticles for diagnosing a cancer that is associated with the EV cancer biomarker. Changes in EphA2-EV blood levels pre- to post therapy also corresponded with therapy responses, suggesting that EphA2-EV blood levels could be used to non-invasively monitor treatment responses. The nPES platform can be used as a rapid, low cost, high throughput, sensitive and specific method for detection and quantitation of EVs in microsample volumes from a variety of sample types. This approach can be readily customized to detect specific disease-derived EV populations for diagnostic assay development, as indicated by our proof-of-concept studies in PC patients.

EXAMPLES

Example 1—Principle and Design of a Purification-Free nPES Platform for EV Detection Gold nanoparticles (GNPs) scatter light at characteristic wavelengths according to their size and shape. For example, 50 nm gold nanospheres (AuS) scatter green light and 25×60 nm gold nanorods (AuR) scatter red light; however, when the distance between AuS and AuR particles is <200 nm their scattering is coupled, forming a plasmon that shifts the spectra of scattered light to yellow while also markedly increasing in scattering intensity (FIG. 1a-f). We applied this principle to design a simple, purification-free nanoplasmon-enhanced scattering (nPES) assay platform to directly detect EVs in micro-samples of different specimen types, including culture media and plasma. For a proof-of-principle demonstration, we used antibodies against CD81, CD63, and CD9, which are enriched on most EV membranes, to both capture and detect all EVs present in a sample. We first conjugated an anti-CD81 antibody to the 116 silica surface of a sensor chip, so that all EVs that express this common EV marker are captured and enriched when the wells of this chip are loaded with samples containing EVs from any cell type. Bound EVs are detected by addition of anti-CD63-AuS and anti-CD9-AuR GNPs to these sample wells, so that dual binding of these two GNP species with immobilized EVs on the chip surface forms AuS-EV-AuR complexes (FIG. 1a). AuS and AuR signals are readily detectable by dark-field microscopy (DFM) (FIGS. 1b and 1c), but AuS-EV-AuR complexes formed after addition of both GNPs produce nanoplasmons that markedly shift the spectra of the scatted light (FIGS. 1d and 1e) and increase signal intensity (FIG. 1f), although this spectral shift is not always apparent due to significant variation in CD63/CD9 expression. Scanning electronic microscopy (SEM) performed to analyze AuS-EV-AuR, AuS-EV and AuR-EV binding and morphology on this sensor chip, detected relatively uniform EV distribution, with readily detectable single and dual GNP binding events.

Example 2—Evaluation of the nPES Platform for EV Detection

To characterize the EV detection performance of this nPES platform, EV samples revealing vesicle morphology and size distributions consistent with pure EV preparations were added to EV-free plasma to create EV plasma standards of known concentration, using nPES area ratios (area of nPES signal vs. well area) to evaluate sample EV concentrations. Negative control assays performed with EV-free plasma revealed very low nPES area ratios (<0.02%), and similar results were found when 150 ng/μL of the EV plasma standard was analyzed on sensor chips without anti-CD81 capture antibody modification (FIGS. 2a and 2b). Experiments performed with only the AuS-anti-CD63 probe exhibited an nPES area ratio of 0.04% (FIGS. 2a and 2b). Markedly different results were observed, however, when anti-CD81-conjugated sensor chips were incubated with this concentration standard and both of the two antibody-conjugated GNPs. Assays performed with both AuS-anti-CD63 and AuR-anti-CD9 exhibited area ratios >0.35% due to nPES signal enhancement (FIGS. 2a and 2b). Reproducibly low non-specific signal in negative control samples and AuS-EV assays, which exhibited only ~10% the signal of AuS-EV-AuR assays, strongly suggested that nPES area ratios should accurately reflect AuS-EV-AuR complex abundance, and thus plasma EV concentrations.

To confirm this hypothesis, we analyzed the sensitivity and linearity of EV values from this nPES assay against those determined by a conventional ELISA. We found that nPES signal increased with EV concentration (FIG. 2c), and that there was a broad linear range (~10-1-104 ng/μL) with a strong correlation ($r2=0.99$) between calculated and known EV concentrations. This nPES assay revealed a 0.07 ng/μL limit of blank and a 0.23 ng/μL limit of detection, while ELISA, the standard quantification method for EVs, failed to detect EV concentrations lower than 10 ng/μL (FIG. 2d).

Figure 2D:
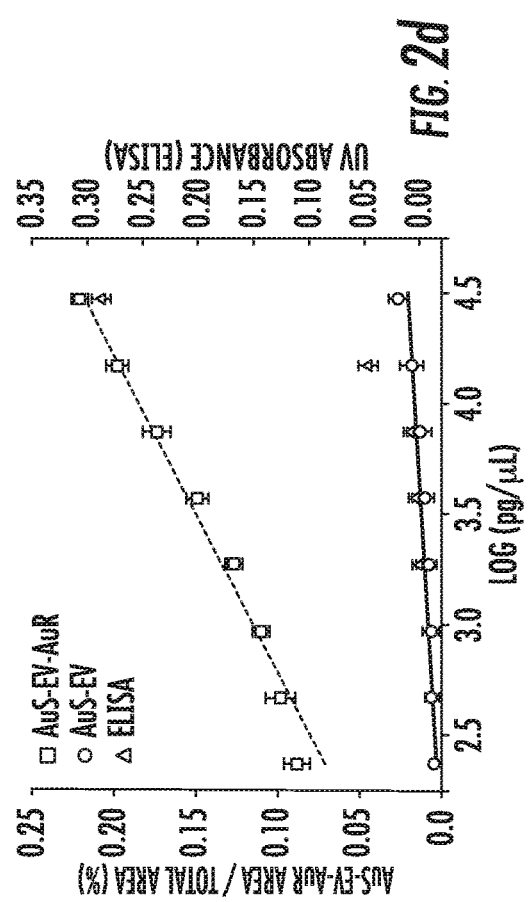
Figure 2A:
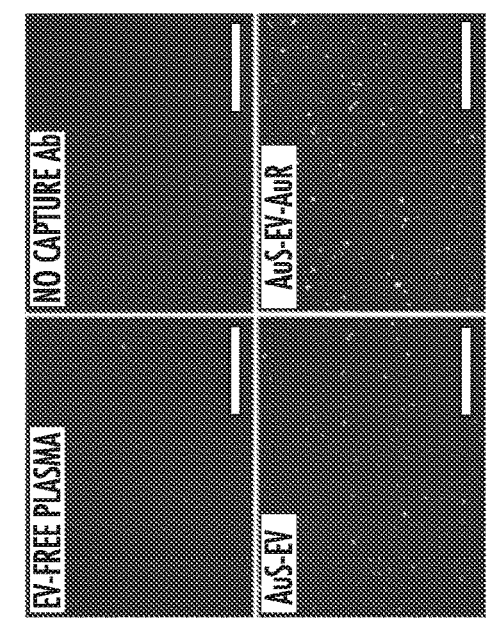
Figure 2C:
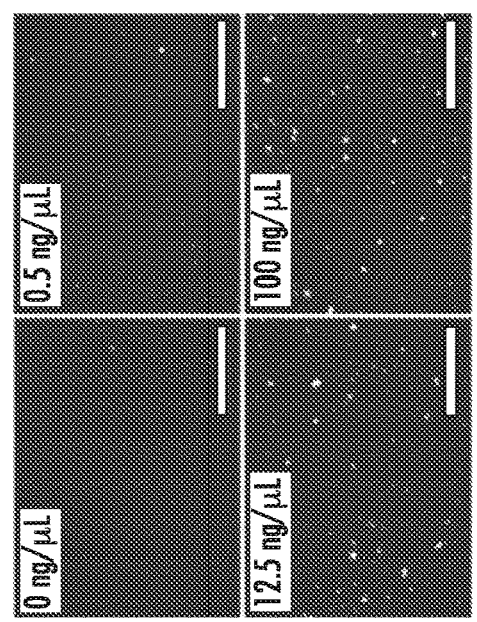

Notably, area ratios generated by AuS-EV-AuR labeling were significantly greater ($p<0.05$) than those generated by single GNP labeling (AuS-EV) at all concentrations and this difference progressively increased with EV concentration (slopes of 0.010 for AuS EV, and 0.069 for AuS-EV-AuR), revealing a signal-amplification plasmon-coupling effect of double-GNP recognition (FIG. 2d). The nPES platform required very little plasma due to its extremely high sensitivity, and unprocessed plasma samples that fell above the assay's linear range (estimated 50 μg/μL) could be diluted >40-fold and still generate signal within this range. We found that 1 μL of plasma was sufficient for these dilutions, performed as well as larger input volumes, and yielded sufficient material for >5 replicate wells using 5 μL of diluted plasma, which exhibited good intra- and inter-assay reproducibility in samples with low and high nPES signal. A comparable ELISA required a pre-purification procedure and a minimum of 50 μL of undiluted plasma for a single replicate well. These ELISAs also cost more than nPES assays ($1.65/well vs. $1.20/well) due to their requirement for prior EV purification and use of larger wells, greater sample volumes and need for an additional enzyme-linked detection antibody and reagents (Table 1). Based on these results, these nPES assays offered multiple advantages over ELISA methods routinely used to measure EV concentrations (Table1).

TABLE 1

Comparison of nPES and ELISA methods.

| | nPES | ELISA* |
|---|---|---|
| Plasma consumption † | 1 μL | 150 μL |
| Isolation step | No | Yes |
| Analysis time ‡ | 5 h | >24 h |
| Limit of Detection | 0.2 ng/μL | 77 ng/μL |
| Dynamic range | 4-5 logs | 2 logs |
| Reagent costs/1000 wells ($) | ~1200 | ~1650 |

*EV ELISAs for CD81/EphA2 expression.
† Assays were performed in triplicate; nPES: 1 μL plasma (diluted 40-fold) yields >5 replicates; ELISA 150 μL undiluted plasma yields 3 replicates
‡ Includes isolation time and detection time.

Example 3—Identification of EV Surface Markers Associated with Pancreatic Cancer Pancreatic cancer is a lethal disease characterized by aggressive local invasion, early metastasis, and a high degree of treatment resistance. Despite its dire prognosis, there are currently no effective noninvasive biomarkers for PC diagnosis. Blood carbohydrate antigen 19-9 (CA19-9) level is the only clinically accepted PC marker but it is of limited use as it is approved only to monitor PC progression or response to therapy. Most PC patients are diagnosed with advanced disease, which usually precludes complete resection to greatly reduce the odds of a favorable treatment outcome. Noninvasive biomarkers that can be effectively employed for early PC diagnosis, and discriminate between PC and chronic pancreatitis, are thus badly needed to reduce cancer morbidity and mortality. PC-derived EVs represent a likely source for such a biomarker, since PC cells differentially express multiple factors, some of which should be present on stably circulating EVs secreted by PC tumors thereby enhancing their detection in the circulation during early stages of PC. Such tumor-derived EVs may represent a relatively small contribution to a complex EV population derived from a wide variety of tissues, however, and thus be difficult to detect with conventional methods, which would require EV purification and subsequent analysis to determine the relative abundance of candidate diagnosis marker in this population. Our nPES assay could theoretically be rapidly adapted to sensitively quantitate tumor-derived EVs directly from patient blood samples, by replacing one of the two EV-specific GNPs with one specific for a membrane protein that is selectively enriched on EVs secreted by tumor cells. Both the conventional and the nPES approach suffer from the same limitation, however, a lack of known tumor-specific EV markers.

Figure 3A:
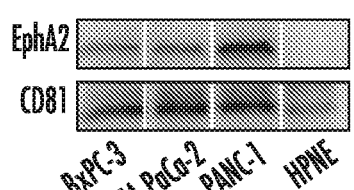
FIG. 3. Identification of PC-associated EV as a potential biomarker by establishing an nPES-EphA2-EV detection system. (a) Western blot analysis of EphA2 expression on EVs from different PC cell lines (BxPC3, MIAPaCa-2, and PANC-1) and a normal pancreas (HPNE) cell line. (b) EphA2-EV and (c) total EV signal in HPNE and PANC-1 culture over time, respectively; n=3 triplicate samples/time point. (d) Quantification of EphA2-EVs and total-EVs (CD81-EphA2-CD9 and CD81-CD63-CD9 nPES assays, respectively), and EphA2-EVs and CD9-EVs (CD9- and CD81-EV ELISAs) in plasma of NC (n=10), pancreatitis (n=10) and PC (n=10) patients. All data is normalized to the corresponding NC sample data. (e) DFM images and (f) EphA2-EV area ratios at indicated time points in plasma samples of nude mice following subcutaneous injection without or with PANC-1 human PC cells (2×106 cells/mouse); n=3 replicates/sample. Data represent means±SEM; p<0.01 and **p<0.0001 vs. control mice and †††p<0.005 and ††††p<0.0001 vs. PC baseline by two-way ANOVA followed by a Sidak multiple-comparison test.

We therefore attempted to identify EV membrane markers to test the ability of a modified nPES assay to detect and quantify tumor derived EVs. We chose PC as our model system, and used an LC-MS/MS-based proteomics and bioinformatics approach to identify transmembrane proteins on EVs derived from human pancreatic carcinoma (PANC-1 and MIA PaCa-2) and pancreatic ductal adenocarcinoma (BxPC-3) cell lines. This approach identified 128 membrane proteins, of which only 26 were expressed on the EVs of at least 2 of the 3 PC cell lines. Of these 26 membrane proteins, only EphA2 exhibited significantly higher expression in Oncomine database (www.oncomine.org) human PC tissue sample than chronic pancreatitis or normal pancreatic tissue samples. EphA2 was also of particular interest due to its reported strong association with cancer progression, metastasis and prognosis. Correspondingly, we found that EphA2 was significantly expressed by EVs from PC cell lines but not EVs from a non-transformed human pancreas cell line (HPNE; FIG. 3a). Based on these results we selected EphA2 as a candidate marker for detection of PC derived EVs (EphA2-EVs).

Figure 3B:
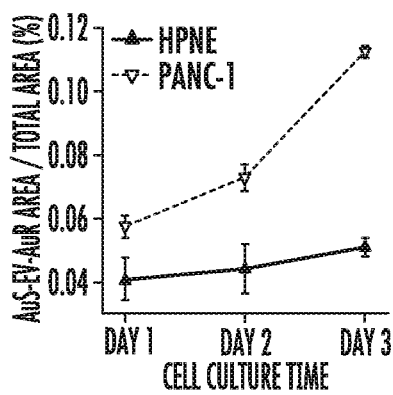
Figure 3C:
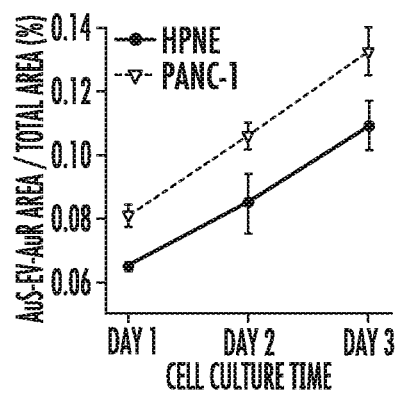
Figure 3D:
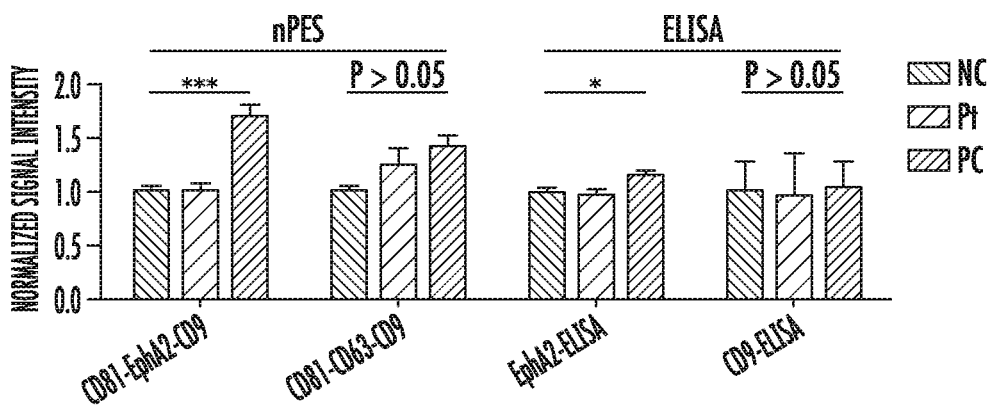
Figure 3E:
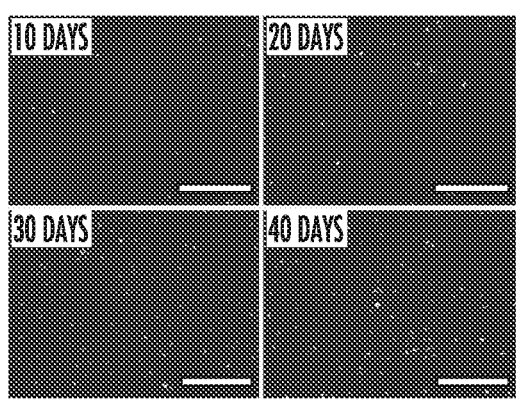
Figure 3F:
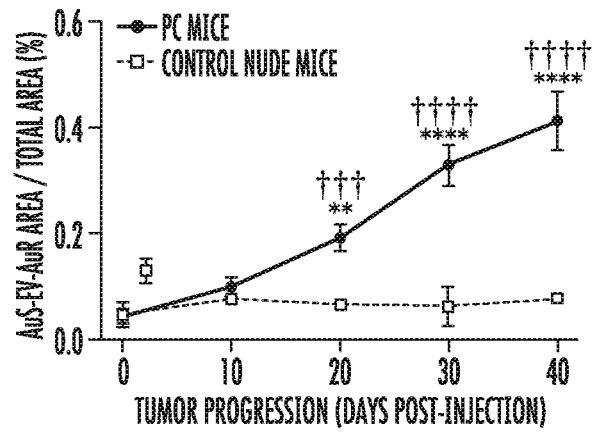

CD81 and CD9 were chosen as the EV capture and recognition targets for our assay since despite the fact that CD63, CD9 and CD81 are all well-known EV marker proteins and CD63 is routinely used for EV capture in many ELISAs, only CD81 and CD9 were expressed on EVs of all pancreatic cell lines analyzed in this study. We therefore established a modified nPES detection system incorporating one capture antibody (anti-CD81) and two antibody-conjugated GNP probes (anti-EphA2-AuS and anti-CD9-AuR), where PC-derived EVs were quantified by recognition of CD9/EphA2 double positive EVs. To evaluate the specificity of the CD81-EphA2-CD9 system for PC-derived EVs, supernatants of cell lines derived from normal (HPNE) or PC tumor (PANC-1) tissue were analyzed at progressive tissue culture time points. EphA2-EV signal was significantly lower in HPNE vs. PANC-1 cell culture supernatants at all time points and did not significantly increase with culture duration, unlike PANC-1 EphA2-EV signal and total EV signal from HPNE and PANC-1 cells, which increased linearly with culture duration (FIGS. 3b and 3c). Plasma samples from normal healthy controls (NC), and pancreatitis and PC patients were also tested to determine the PC specificity of the EphA2-EV (CD81-EphA2-CD9) and general-EV (CD81-CD63-CD9) detection and quantification systems. EphA2-EV signal was significantly higher in plasma samples of PC vs. pancreatitis patients or NC subjects ($p<0.001$), who had similar EphA2-EV signals (FIG. 3d), while general-EV signal was not significantly different among these groups, nor were EV-CD9 ELISA values. EphA2 EV increases were also observed between these samples when we employed a custom EphA2 EV ELISA, although this assay required EV pre-isolation and detected much smaller differences (FIG. 3d). Calculations based on NanoSight, ELISA and nPES assay data determined that EphA2-EVs represented approximately 0.15% and 0.26% of total plasma EVs in NC and pancreatitis samples, respectively, and 5.93% of plasma EVs in PC patient samples. To address the ability of the nPES CD81-EphA2-CD9 system to detect EphA2-EVs during PC tumor development, athymic nude mice permissive for tumor growth were injected with PANC-1 PC cells and analyzed for EphA2-EV blood levels every 10 days post-injection. EphA2-EV plasma levels remained stable in control mice ($P>0.5$ for difference at any time point), but increased with time in mice injected with PC tumor cells, significantly diverging from both baseline and control mice by 20 days post-injection (FIG. 3f), and highly correlated ($R2>0.60$) with tumor size.

Example 4—Evaluation of EphA2-EV for Early PC Detection and Monitoring Treatment Responses To investigate whether nPES EphA2-EV detects early PC cases, we analyzed EphA2-EV signal in plasma samples drawn from a larger cohort which included PC patients with early-stage disease (PC stage I and II) who could still potentially benefit from curative surgical resection. None of these groups significantly differed by age or gender, while plasma levels of the non-diagnostic PC biomarker CA19-9 differed between PC vs. NC and pancreatic patients, but not when these patients were segregate by early (stage I+II) and late (stage III) tumor stage. Similar to previous results, plasma EphA2-EV levels were significantly 254 higher in PC than pancreatitis and NC cases. Further, EphA2-EV levels of early-stage PC patients (stage I and II) were also significantly higher than those of the pancreatitis ($p<0.001$) and NC cases (FIG. 4a, $p<0.001$). These results indicated a strong association between circulating EphA2-EV and PC, including early-stage PC, suggesting the potential utility of EphA2-EV as an early PC detection marker. Similar comparisons were also performed for plasma CA19-9 levels, which are clinically approved as means of monitoring a patient's disease progression and therapy response but not for PC diagnosis or staging. CA19-9 levels were significantly increased in PC vs. pancreatitis and NC plasma samples, but not early-stage PC samples, although there was extensive overlap across all these groups which would reduce the discriminatory power of this assay for PC diagnosis. Receiver operating characteristic (ROC) curves indicated that plasma EphA2-EV level was an excellent classifier for differentiating PC cases, including early-stage PC, cases from pancreatitis and NC cases (FIG. 4b-i; AUC 0.93-0.96), performing significantly better than CA19-9 ($p<0.001$). Plasma EphA2-EV sensitivity for PC vs. NC (94%) or pancreatitis (89%) cases was significantly better than CA19-9 (81% and 61%, respectively). Notably, EphA2-EV discriminatory sensitivity was only modestly diminished for early-stage (stage I-II) PC vs. NC (91%) or pancreatitis (86%) comparisons, further demonstrating the potential of EphA2-EV as a promising early-detection marker for PC.

PC cases are frequently characterized by high rates of therapy resistance, and improved means of monitoring therapy responses are urgently needed to allow rapid modification of personalized treatment regimens in order to improve patient outcomes. We thus investigated whether plasma EphA2-EV levels reflected PC tumor responses to neoadjuvant therapy. Plasma samples were collected from 23 PC patients before and after neoadjuvant chemotherapy and/or chemoradiation, and stratified according to patient responses to neoadjuvant therapy. Post-therapy EphA2-EV levels significantly decreased in patients with good/partial therapy responses (<50% viable tumor cells post-therapy), but not in patients with poor responses (>50% viable tumor cells post-therapy) (FIG. 4j-1), while CA19-9 levels in these samples did not significantly differ by treatment response. Changes in EphA2-EV levels are thus strongly associated with treatment response, and perform better than CA19-9 levels, which are sometimes used for clinical evaluation of PC treatment responses. EphA2-EV levels may thus be a useful independent indicator to monitor PC patient responses to therapy.

DISCUSSION

Conventional protein biomarkers are often subject to variable regulation by non-specific factors, such as blood hydrolases, that can significantly impact their levels in the circulation. Biomarker detection can also be impaired by non-specific competition from abundant proteins and peptides in blood, particularly in early stages of diseases when biomarker levels are low. EV-based assays may be less affected by these confounding influences, since membrane-bound or membrane-enclosed EV biomarkers are likely to be at least partially protected from hydrolysis and more easily separated from abundant non-specific proteins than target proteins that are not physically constrained by a vesicle membrane. Such advantages may be particularly important for detection of early disease states when low biomarker levels are likely more susceptible to degradation or masking interactions.

EVs are increasingly recognized as a potentially valuable source of new diagnostic biomarkers, but current EV analysis techniques require complex and lengthy isolation procedures and their volumes requirements limit their use with common mouse models of human disease and preclude longitudinal studies. Sensitive detection and quantification of EVs associated with specific disease states, without need for a separate pre-purification step is highly desirable for both research and clinical applications. For example, a recently report described a surface plasmon resonance sensor method that can distinguish healthy and pancreatic cancer patients based on exosomal microRNAs isolated from patient blood samples; however, this method required both EV and RNA isolation prior to sample analysis and thus is not suitable for high-throughput clinical analyses.

Our nPES platform integrates EV capture and detection, using a plasmon-coupling effect to achieve dual increases in detection sensitivity and specificity to allow rapid, ultrasensitive biomarker quantification in small sample volumes. Notably, we achieved robust assay reproducibility using 1 μL of plasma samples. This ability to use small sample volumes may be particularly valuable in clinical or research settings where samples are subject to volume constraints and often required for multiple analyses. For example, the microsample volumes required for this assay permit multi-sample mouse time course studies, which have not previously been feasible due to the large volume requirements of conventional EV analysis methods. This should greatly benefit studies using mouse models to monitor EV changes associated with tumor or disease progression and corresponding therapy responses.

The EV nPES platform we describe should be generalizable to any disease state associated with a specific EV marker. We selected PC as a proof-of-principle model in this study, using proteomics and bioinformatics to identify a candidate PC-specific EV membrane biomarker for use as the disease-specific probe in a customized nPES assay. We found that EphA2 was highly enriched on EVs of PC cells but essentially absent on EVs of normal pancreas cells, and therefore chose EphA2 as a PC-selective EV biomarker for our assay. EphA2 overexpression is not restricted to PC tumors, however, as it is also overexpressed in the early stages of colorectal cancer and non-small cell lung cancer, suggesting its potential as a target for early cancer detection, and accumulates during tumor progression, interacting with downstream cancer-associated signaling pathways to promote malignant cell growth and invasiveness. Results of the present study illustrate the early diagnostic power of EphA2-EV for PC, and its potential to detect other forms of cancer should be addressed by future studies. If necessary, the cellular origin of EphA2-EVs, or other disease-associated EVs, could be addressed by replacing the EV-specific anti-CD9-AuR probe with a cell-specific AuR probe. Similarly, EV-markers associated with a particular mutation or phenotype could be assessed by replacing the anti-CD9-AuR probe or by parallel assays using an additional set of probes.

Studies were performed with PC patients, since this disease is characterized by aggressive local invasion, early metastasis, and high rates of therapy resistance, and there are currently no FDA-approved, non-invasive assays for PC diagnosis, and only one relatively non-specific biomarker, CA19-9, for evaluation of patient responses to therapy. Due to its nonspecific symptoms, aggressive nature and the lack of effective strategies for early detection, 80%-85% of PC patients are diagnosed with advanced disease, precluding surgical resection, the only available cure. We therefore evaluated ability of our nPES EphA2-EV assay to discriminate PC patients with early disease (stage I/II), who could still potentially benefit from curative surgical resection, from NC and pancreatitis cases. Pre-therapy EphA2-EV blood levels accurately distinguished stage I/II PC patients from NC (AUC=0.96) and pancreatitis patients (AUC=0.93), performing much better than similar comparisons using circulating CA19-9 levels, sometimes used as an initial non-FDA-approved screening method in a PC diagnosis. We thus propose that an nPES EphA2-EV blood assay may have significant value as PC screening test, since a rapid, accurate, non-invasive and inexpensive blood test for early PC diagnosis could improve early detection rates to improve patient outcomes, although we acknowledge that this would require more imaging studies and/or biopsies to rule out false positive results.

Low neoadjuvant therapy response rates are a major factor in poor PC patient outcomes. Circulating CA19-9 levels are sometimes used to monitor treatment responses, but more sensitive and specific non-invasive markers are needed to guide the design of more effective personalized therapy regimens. Our results suggest that an nPES EphA2-EV blood assay be used to monitor therapy responses of PC patients, as EphA2-EV blood levels significantly decreased in patients that revealed good/partial but not poor therapy responses.

The nPES approach described herein offers an attractive means for rapid, purification-free and ultrasensitive measurement of circulating EVs in small sample volumes. The results of our proof-of-concept study demonstrate promising translational implications and suggest important avenues for future research. Noninvasive nPES EphA2-EV analyses could improve early PC detection and treatment monitoring, but larger prospective studies are required to validate these results. The nPES platform should also be readily customized to diagnose and monitor other cancers and infections by replacing one or both probes with disease-of cell-type-specific EV markers. Further, while the image capture and analysis aspects of this assay have already been automated, and can be directly translated to a clinical setting, minor changes to increase assay capacity and automation should allow high-throughput detection for improved clinical translation.

Materials and Methods

Experimental Design.

This translational study was designed to establish and characterize a rapid, purification-free three probe EV quantification assay that could be modified by addition of pancreatic cancer-specific EV probe to allow high-sensitivity and high-specificity diagnosis of early and late stage pancreatic cancer from small blood samples. Cancer-derived EVs are of great interest as potential diagnostic markers, but few cancer specific EV markers have been identified and most current EV assays are labor-intensive and low-throughput, rendering them impractical for clinical use. We therefore attempted to develop a three probe EV capture and detection system, where a capture antibody recognizing an EV membrane protein (anti-CD81) was used to enrich EVs within a sensor well, while antibody-conjugated gold nanorods and nanospheres recognizing two additional EV membrane proteins served as EV probes. This approach was designed so that binding of the different gold nanoparticle species on an EV would form a plasmon to shift the wavelength and increase the intensity of scattered light under dark field illumination to improve the sensitivity and specificity of EV detection. We next used comparative proteomics to identify membrane proteins with known cancer associations that were selectively enriched on EVs of human pancreatic carcinoma or ductal adenocarcinoma cell lines as candidates for a PC specific EV probe. In order to demonstrate the feasibility of this approach, a probe against this marker was included in our three probe assay, which was then tested for its sensitivity and specificity for PC EVs in cell culture supernatants; pre-treatment blood samples of a small cohort of 10 PC, 10 pancreatitis and 10 control patients; or longitudinal blood samples of mice injected with a human PC cell line. We next examined assay performance in a larger, independent cohort of 59 PC, 48 pancreatitis and 48 control patients, its ability to distinguish early PC disease stages from pancreatitis and control patients, and its performance against another commonly PC marker, CA 19-9, which is not FDA-approved for PC diagnosis or cancer staging. Finally, we analyzed whether assay values reflected PC tumor responses to neoadjuvant therapy using blood samples collected from 23 PC patients before and after neoadjuvant therapy, and stratified according to patient responses to treatment, comparing results to CA 19-9 expression to assess assay non-inferiority.

Cell Culture.

The human PC cell lines PANC-1, MIA PaCa-2, BxPC-3, and the human pancreas cell line HPNE were obtained from the American Type Culture Collection (Manassas, VA). PANC-1 and BxPC-3 cells were cultured in RPMI-1640 medium (Hyclone, GE Healthcare Life Sciences), MIA PaCa-2 cells were cultured in DMEM/high-glucose medium (Hyclone, GE Healthcare Life Sciences), and HPNE cells were cultured in minimal essential medium (MEM, Hyclone, GE Healthcare Life Sciences) with 10% FBS. All cultures were supplemented with 10% fetal bovine serum (FBS, Life technology, Thermo Scientific Inc.), penicillin (1 U) and streptomycin (1 µg/mL) and incubated at 37° C. in a humidified 5% CO2 incubator. All cell lines were cultured in triplicate under the same conditions and then harvested to collect independent EV samples.

Clinical Samples.

PC, pancreatitis, and NC subject plasma samples from a small trial cohort (n=10/group) and a larger validation cohort (n=48-49/group) were collected at the time of diagnosis by the department of pathology and genomic medicine at Houston Methodist Hospital after approval by the Institutional Review Board (IRB0213-0011). Based on data from the trial cohort, chi-square power analysis (PASS V08.0.3, Kaysville, UT) indicated that we required at least 47 clinical specimens per group to detect an effect size of 30%, with an alpha of 0.05 of and 90% power. PC samples used for treatment evaluation, and demographic information, treatment history, and response to therapy were obtained from 23 PC patients undergoing treatment at MD Anderson Cancer Center. Plasma samples were collected from these PC patients 1-2 months before and after neoadjuvant chemotherapy and/or chemoradiation. All patients gave written informed consent for study participation (IRB PA11-0670 and IRB PA14-0646). Treatment response was assessed by pathologists at MD Anderson as part of the routine diagnostic evaluation, using a grading system based on the criteria proposed by Evans et al to evaluate the extent of residual tumor. The investigators were not blinded to the group identities of the clinical samples during sample analysis.

Preparation of EV Concentration Standards.

Plasma samples were centrifuged at 110,000 g overnight, and supernatants were collected as EV-free plasma, and analyzed by Western blot analysis, which found that the EV marker proteins CD63 and Tsg101 were markedly depleted in EV-free plasma supernatants, but highly enriched in the matching plasma precipitates. Standard EV samples of known mass isolated from pooled human serum (System Biosciences Inc.) were dissolved in EV-free plasma to a final concentration of 1 µg/µL, and further diluted to required concentrations (30000, 15000, 7500, 3750, 1870, 938, 469, 234 µg/µL) by 2-fold dilution with EV-free plasma at time of use.

EV Isolation from Culture Media.

Cells were grown in culture media with 10% FBS for at least 48 h, washed three times with PBS (pH 7.0), and then cultured for 48 h in serum-free media. Culture supernatants were then collected and centrifuged at 400 g for 15 min to pellet cells, centrifuged at 8,000 g for 40 min to remove cell debris, concentrated with 10 kDa centrifugal filtering units (Merck Millipore Ltd.) and then centrifuged at 110,000 g for 90 min. Precipitates were carefully collected, resuspended in PBS (pH 7.0), and then centrifuged at 110,000 g for 90 min. Resulting EV precipitates were collected, dissolved in 200 µL PBS (pH 7.0), and stored at 4° C.

Plasma EV Isolation for ELISA.

Total EVs in plasma were isolated using the ExoQuick kit (SBI Inc.). Briefly, 10 µL of ExoQuick reagent was added to 50 µL plasma. After gentle shaking, the mixture was incubated for 1 h in an ice bath, then centrifuged at 20,000 g for 30 min and the resulting EV precipitates dissolved in 100 µL PBS (pH 7.0) with ultrasonication.

ELISA Assays.

Ninety-six-well plates first incubated with anti-human CD81 antibodies (0.2 µg/mL in PBS; R&D Systems, clones #454720) for 12 h at 4° C. After carefully washing with PBS, the plate was incubated for 4 h at 25° C. with EVs (100 µL/well) isolated from cell culture media or plasma, aspirated and incubated at room temperature for 4 h with 5% BSA in pH 7.0 PBS (100 µL/well), washed three times with 0.01% Tween-20 in PBS (PBST, pH 7.0), and incubated for 1 h at 37° C. with 100 µL/well anti-human CD9 or EphA2 antibodies (0.2 µg/mL in 5% BSA/PBS; R&D Systems, clones #209306 and #371805). Wells were then washed five times with PBST, incubated for 0.5 h at 37° C. with a 1:5,000 dilution of HRP-conjugated secondary antibody (Cell Signaling Technology) in 5% BSA/PBST (100 µL/well), washed five times with PBST, incubated for 10-15 min at 37° C. with 100 µL/well of TMB reagent (eBioscience Inc.), and then supplemented with 50 µL/well of stop solution (2 M H2SO4) and analyzed for absorbance at 450 nm. The standard curve was calculated using Origin 8.0 software (OriginLab) plotting light absorbance versus the log 10 EV standard concentration in pg/µL.

LC-MS/MS Proteomics Analyses.

EV samples incubated with M-PER mammalian protein extraction reagent (Thermo Scientific Co.) to purified EV solution for 30 min in an ice bath and extracted protein concentrations were measured with a bicinchoninic acid (BCA) assay, (micro BCA Kit, Thermo Scientific). Protein extracts were diluted to 1 µg/L with 100 mM NH4HCO3, supplemented with 10 mM dithiothreitol, incubated at 37° C. for 1 h, supplemented with 30 mM iodacetamide, incubated in the dark for 30 min at room temperature, then supplemented with 1 µg trypsin and incubated and incubated overnight at 37° C. Protein hydrolysis was arrested by addition of 0.1% trifluoroaceticacid and peptide solutions 481 were diluted to 0.25 µg/µL with H2O/acetonitrile (95:5), centrifuged at 21,000 g for 20 min, and supernatants directly subjected to LC-MS/MS analysis.

Peptides were separated using an ultimate 3000 nano-LC (Thermo Scientific Co.) equipped with a C18 Pepmap 100 enrichment column (Thermo Scientific; 5 μm particle size, 100 Å pore size, 300 m i.d.×5 mm) and a C18 Pepmap 100 analytical column (Thermo Scientific; 3 m particle size, 100 Å pore size, 75 m i.d.×150 mm), using flow rates of 20 L/min and 300 nL/min for the loading and analytical columns, respectively. Eluted peptide fractions were analyzed by a Velos Pro Dual-Pressure Linear Ion Trap Mass Spectrometer (Thermo Scientific). One MS scan was followed by eight MS/MS scans. All of the MS/MS spectra were used to search Mascot 2.3.0 (www.matrixscience.com), using a measurement tolerance on of 0.5 Da.

Antibody Modification of Gold Nanoparticles (GNPs).

Modifications of gold nanosphere (AuS) and nanorod (AuR) with different antibodies followed similar procedures. Briefly, 40 μL of carboxyl functionalized gold nanoparticles (GNPs; 9×10–10 M, Ocean NanoTech) were mixed with 20 μL MES buffer (pH 4.7, Ocean NanoTech), then mixed with 20 μL of EDC/sulfo-NHS solution (Sigma-Aldrich; 2 mg/mL 1-ethyl-3-[3-dimethylaminopropyl]carbodiimide hydrochloride (EDC) and 1 mg/mL N-hydroxysulfosuccinimide (sulfo-NHS) in MES buffer), incubated for 10 min at room temperature, and successively supplemented with 80 L coupling buffer (Ocean NanoTech) and 20 μL antibody solution (0.5 mg/mL; R&D Systems, clones #371805 (ant-EphA2), #209306 (anti-CD9) and #460305 (anti-CD63)) then shaken for 2 h at room temperature to complete the coupling process. The reaction was then stopped with 2 L of quenching buffer (Ocean NanoTech), and centrifuged for 10 min at 6,000 rp Precipitated GNPs were washed three times with 400 μL washing buffer (Ocean NanoTech), and then resuspended in 40 μL washing buffer and stored at 4° C.

Construction of an nPES Platform for EV Quantification.

Amino group functionalized glass slides (NH2-glass, Nanocs Inc.) were ultrasonically cleaned in methanol for 5 min, thoroughly flushed with deionized water, dried under an N2 stream, and then the NH2-functionalized glass was covered with a 50 well polydimethylsiloxane membrane (CW-50R-1.0-CultureWell Gasket, Grace Bio-Labs Inc.). Slides were filled with 10 μL/well of 12.5 μg/mL anti-human CD81 antibody (R&D systems, clone #454720) in 5 mM EDC/PBS and incubated at room temperature for 2 h in a moist chamber, aspirated and filled with 10 μL/well of 5% BSA/PBS (pH 7.0) and incubated at room temperature for 4 h, then PBS (pH 7.0) washed and aspirated three times prior to loading these wells with analysis samples. Sample wells were filled with 5 μL/well of plasma samples (diluted 40 with pH 7.0 PBS) or cell culture EV samples, incubated at room temperature for 4 h in a moist chamber, washed three times with PBST, three times with PBS and then filled with 7 μL/well of AuS and AuR PBST probe solution ($4 \times 10^{-11}$ M for each particle) and incubated for at room temperature for 1 h, after which the PDMS cover was removed, the slide was washed three times with PBST and three times with PBS, then fitted with a cover slip and imaged by dark-field microscopy (DFM).

DFM Imaging and Scattering Spectroscopy Measurements.

DFM images were acquired on an inverted microscope (Olympus IX71, Olympus Co.) equipped with a 100 objective lens (NA, 0.8) and a dark-field condenser (0.8<NA<0.95). The scattered light from a 100 W halogen lamp was recorded by an Olympus DP70 digital camera to generate dark-field color images and by a spectrograph CCD equipped with a monochromator (CASCADE 512B, Roper Scientific.) to obtain scattering spectra (integrated over 10 s) of selected AuS, AuR and AuS-AuR particles in wells.

NIH IMAGE J image analysis software was used to analyze DFM images. DFM AuS-EV-AuS signal was quantified using a pixel intensity threshold of 255 to exclude AuS-EV signal detected at lower thresholds, since this cut-off was found to detect <0.4% of AuS-EV spots and 0% of AuR-EV spots in 20 EV wells incubated with both AuS and AuR probe, where false positive AuS-EV signal accounted for <0.2% of the total AuS-EV-AuR signal.

DFM images were processed with the NIH Image J software with the color threshold set as hue 0, saturation 0, and brightness 255. Image areas with brightness equal to 255 were software-selected, and the ratio of these areas to those of the whole image were calculated by the software to give area ratios indicating specific nPES EV signal. Linear regression of nPES area ratio with log 10 EV concentration was used to generate the standard concentration curve for derivation of experimental EV concentrations.

Mouse PC Models.

Six- to eight-week-old male nude mice (Crl:NU-Foxnlnu) purchased from Charles River Laboratories (Wilmington, MA) were housed in Houston Methodist Research Institute (HMRI) animal facilities in accordance with institutional animal care and use committee (IACUC) guidelines. All animal procedures followed HMRI policies and IACUC-approved protocols. Three mice were subcutaneously injected in the left flank with 2×106 PANC-1 cells suspended in 100 μL of PBS to establish subcutaneous pancreatic tumors63 and compared to three healthy control mice that did not receive tumor cell injections. Mouse retro-orbital blood samples for analysis of EphA2-EV plasma levels and tumor size data were collected at 0, 10, 20, 30, and 40 days post-injection. Calipers were used to determine tumor length and width, and tumor volume was estimated using the modified ellipsoid volume formula (½ length× width$^2$). Investigators were not blinded to the group identity of the animal samples during nPES analyses.

Western Blots.

Western blot analyses were performed with 10 μg EV protein lysate and precast Mini-PROTEAN TGX gels and polyvinylidene difluoride membranes (Bio-Rad) using standard methods.

Measurement of Method Repeatability.

Assay reproducibility was assessed using two randomly selected samples that were analyzed in three assays with 20 replicates that were performed on three separate days to generate 60 values per sample. Resulting values were used to calculate intra- and inter-assay means and coefficients of variation (% CV).

SEM Image Analysis.

SEM images of GNP binding to EVs were generated using EVs purified from 50 μL of human plasma with ExoQuick kits to reduce SEM artifacts. Purified EVs were immobilized on sensor chips and hybridized with anti-CD63-AuS and anti-CD9-AuR, as described above. Sensor chips were then PBS (pH 7.0) washed, dried under a gentle N2 stream, then treated with a direct current sputter coating approach to apply a 3 nm layer of iridium and imaged with a NOVA NanoSEM 230 microscope (FEI) at a 5 kV acceleration voltage in high vacuum ($3 \times 10^{-6}$ Torr) using a 5 mm working distance. Three randomly selected 80-120 μm2 SEM fields were analyzed to calculate the number of total and GNP-bound EVs per μm2 for each assay.

EV Concentrations in Patient Plasma Samples.

A NanoSight LM10 instrument and Nanoparticle Tracking Analysis software (Malvern Instruments) were used to measure total-EV concentrations in pooled patient plasma samples (10 PC, 10 Pt, and 10 NC samples). Estimates of total-EV protein/μL plasma were determined by BCA assay of EVs isolated from pooled plasma samples with ExoQuick kits. The nPES assay standard curve equation (nPES signal intensity=0.069×Log 10 [EphA2 EV concentration]−0.093) and mean EphA2 nPES signal intensity data from 10 samples in each patient group was used to calculate estimates of the plasma EphA2-EV protein content for each group (EphA2 EV concentration=$10^{(nPES\ intensity+0.093)/0.069}$). The EphA2-EV percentage of Total-EVs in each patient group was calculated as the ratio of EphA2-EV to total-EV protein content. Total-EVs per assay well were calculated as the input volume of diluted plasma sample (5 μL of 40× diluted plasma) and EphA2-EVs per well as the fraction of EphA2-EVs/Total-EVs.

Statistical Analysis.

GraphPad Prism version 5.0 (GraphPad Software) and MedCalc statistical software version 13.0 (MedCalc Software bvba) were used for all calculations. The MedCalc was used to create heat maps of patient nPES EphA2-EVs levels. Statistical analyses were performed using Student's t-tests, one-way ANOVAs with Bonferroni's post-test or Kruskal-Wallis one-way ANOVA with Dunn's post-test as determined by sample distribution and variance. Differences with p-values<0.05 were considered statistically significant. ROC curves were used to determine sensitivity and specificity, with the optimal cut point defined as the point of closest approach to the upper left axes according to the following criterion: min [$(1-sensitivity)^2+(1-specificity)^2$]. Figures were prepared using GraphPad Prism (GraphPad) and Origin software (OriginLab). All data points are derived from three or more biological or technical replicates as indicated for each experiment.

What is claimed is:

1. A method of detecting a cancer specific protein that is enriched on an extracellular vesicle (EV), comprising:
    contacting a sample comprising the EV with a surface conjugated with a first antibody directed to a first molecule on the EV to capture the EV on the surface;
    removing the remainder of the sample from the surface to generate separated EV captured on the surface;
    incubating the separated EV captured on the surface with a first set of nanoparticles conjugated with a second antibody directed to the cancer specific protein on the EV and incubating the separated EV captured on the surface with a second set of nanoparticles conjugated with a third antibody directed to a second molecule on the EV, wherein the first molecule and the second molecule are selected from the group consisting of CD63, CD81, CD9, CD24, CD26, CD10, tumor susceptibility gene 101 (TSG101), heat shock 70 kDa protein 4 (HSP70), Rab-5b, programmed cell death 6-interacting protein (AIP1/Alix), aquaporin 2 (AQP2), vascular endothelial growth factor receptor 1 (FLT1), N-glycan containing a fucose residue, phosphocholine, phosphatidylserine, and sphingomyelin; and
    detecting whether said cancer specific protein is present in the sample by detecting binding between the second antibody and the cancer specific protein on the EV, wherein dual binding of the two antibody-conjugated nanoparticles to the EV produces nanoplasmons and said nanoplasmons are detected,
    wherein the cancer specific protein is ephrin type-A receptor 2 (EphA2), and wherein the EphA2 is associated with pancreatic cancer.

2. The method of claim 1, wherein the nanoparticles comprise a plurality of nanospheres, a plurality of nanorods, or a combination thereof.

3. The method of claim 2, wherein the detecting step comprises detecting binding between the second antibody and the EV and detecting binding between the third antibody and the EV.

4. The method of claim 2, wherein the nanoparticles comprise gold.

5. The method of claim 2, wherein the first antibody is different from the third antibody.

6. The method of claim 2, wherein the first antibody is the same as the third antibody.

7. The method of claim 2, wherein the second antibody is different from the third antibody.

8. The method of claim 2, wherein the first nanoparticle is different from the second nanoparticle.

* * * * *